(12) United States Patent
Solingen

(10) Patent No.: US 6,589,259 B1
(45) Date of Patent: Jul. 8, 2003

(54) MEDICAL INSTRUMENT, PARTICULARLY A SURGICAL INSTRUMENT

(75) Inventor: Simon Solingen, Los Angeles, CA (US)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/473,502

(22) Filed: Dec. 28, 1999

(51) Int. Cl.⁷ .............................................. A61B 17/32
(52) U.S. Cl. ...................................................... 606/170
(58) Field of Search ............................... 606/170, 171, 606/174, 180, 205, 209, 210

(56) References Cited

U.S. PATENT DOCUMENTS

| | | | |
|---|---|---|---|
| 4,122,856 A | * | 10/1978 | Mosior et al. ............... 606/170 |
| 5,490,861 A | * | 2/1996 | Kratsch et al. ............. 606/174 |
| 5,496,347 A | * | 3/1996 | Hashiguchi et al. ........ 606/205 |

FOREIGN PATENT DOCUMENTS

DE  197 31 453 C2  7/1999

\* cited by examiner

Primary Examiner—Kevin T. Truong
(74) Attorney, Agent, or Firm—St. Onge Steward Johnston & Reens LLC

(57) ABSTRACT

The invention relates to a medical instrument, particularly a surgical instrument with a displaceable push/pull rod arranged on the proximal end of a hand manipulator for activating remote tool parts on the distal end, in which a force-limiting device is envisaged for limiting the transmission of force onto the remote tool parts from the hand manipulator via the push/pull rod. In order to design a simple and cost effective force-limiting device the push/pull rod is designed to be spring elastic in its lateral length.

12 Claims, 2 Drawing Sheets

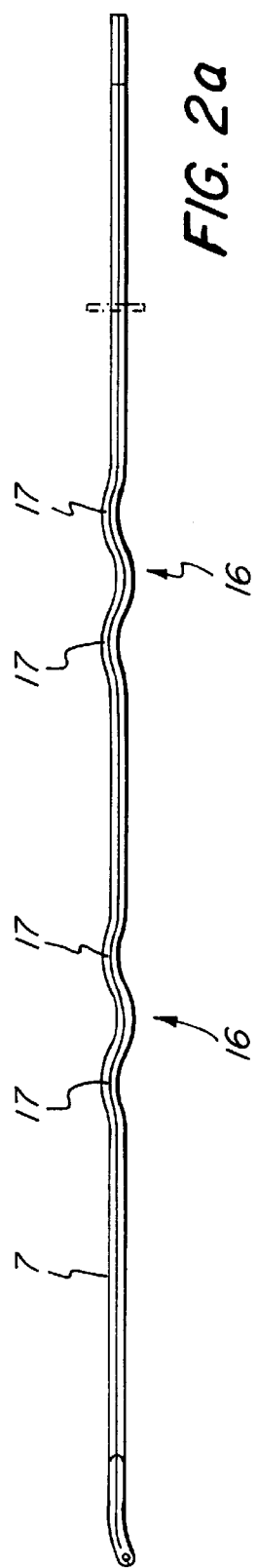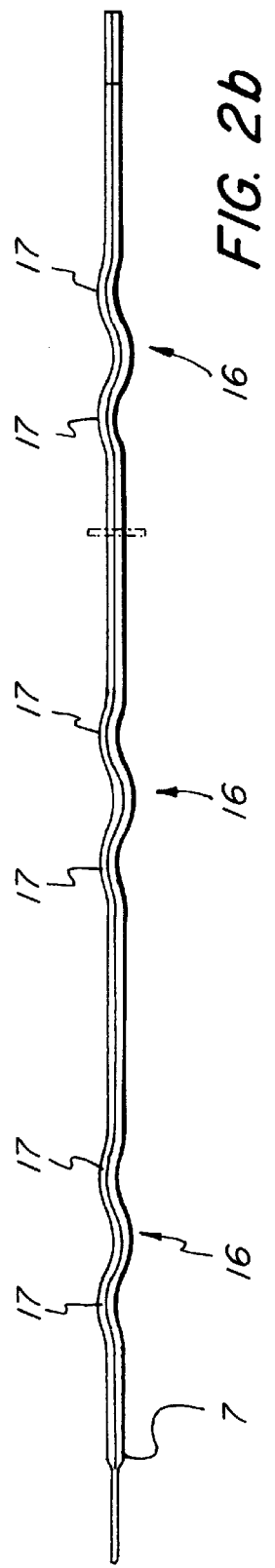

MEDICAL INSTRUMENT, PARTICULARLY A SURGICAL INSTRUMENT

BACKGROUND OF THE INVENTION

The invention relates to a medical instrument, particularly a surgical instrument with a displaceable push/pull rod arranged on the proximal end of a hand manipulator for activating remote tool parts on the distal end, wherein a force-limiting device is envisaged for limiting the transmission of force from the hand manipulator onto the remote tool parts via the push/pull rod.

FIELD OF THE INVENTION

This kind of medical instrument can for example be a needle holder, a gripping-, holding- or preparation tool, scissors or other instrument, in which the push/pull rod can be moved back and forth using manual force via the hand manipulator, in order to move, i.e. to open and close, the remote tool parts which are predominantly open-ended tool parts.

DESCRIPTION OF THE RELATED ART

These known medical instruments available in various embodiment configurations have a long hollow cylindrical shaft, onto the distal end of which the remote tool parts are arranged. The hand manipulator with a rigid handle element and a swivelling handle element is arranged on the proximal end of the shaft. To activate the remote tool parts via the hand manipulator, the remote tool parts and the swivelling handle element of the hand manipulator are coupled via the push/pull rod which is located in the hollow cylindrical shaft. In this way it is possible to open and close the remote tool parts by counter-adjusting.

These types of medical instruments are often used during minimally invasive surgery where they are introduced into the patient's body using trocars. Due to the miniaturisation of the instruments required for minimally invasive surgery, the instruments are more sensitive to pressure since, due to miniaturisation, the individual components can only absorb marginal forces, which for example are brought about by hand pressure upon activating the hand manipulator. In the case of the type of medical instruments mentioned earlier, the swivel handle element of the hand manipulator is designed as a lever, wherein the hinge axis of the two handle elements form the lever axis. The distance from the hinge axis to the point at which the push/pull rod is located on the handle element is considerably shorter than the distance from the hinge axis to the finger hole on the end of this handle element. The transmission ratio is generally around 10:1, that is, the standard closing force of the hand of about 100 N is amplified tenfold due to mechanical leverage, is to around 1,000 N.

When using these medical instruments in practice, in particular the gripping and holding tools, the aim is to generally hold an object, for example a swab or a needle and to place it securely and firmly between the remote tool parts. Strong people can exert a closing force onto the hand manipulator of about 150 N or more, which is then amplified to 1,500 N or more due to mechanical leverage. Frequent use of excess pressure on the remote tool parts can lead to material fatigue or even to the remote tool parts fracturing, whereupon loss of small parts in the operating arena particularly during an operation can lead to the patient getting injured.

In order to avoid undue excess forces being exerted onto the push/pull rod via the hand manipulator and therefore onto the remote tool parts, a force-limiting device is known in the practical field in which the transmission of force between the hand manipulator and the push/pull forces and/or the remote tool parts is limited by a force-limiting device. This type of force-limiting device is known for example from DE 197 31 453-C2. With this known device the push/pull rod is designed as a two-piece component, in which both the push/pull rod sections are connected to one another by way of a force-limiting device. One section of the rod is designed with a casing comprising an internal steepening flat body wedge across the direction of movement of the push/pull rod. The other rod section has a tapered cone with a corresponding flat body wedge of the casing upon being subjected to tensile pressure of the push/pull rod, through which a portion of the closing force generated is absorbed, so that no further undue excess pressure can be exerted onto the remote tool parts.

In accordance with another known embodiment configuration the force-limiting device is designed as a spring assembly on the proximal end of the push/pull rod and which absorbs a portion of the force transmitted onto the push/pull rod via the hand manipulator.

All these state of the art known force-limiting devices have indeed proven themselves in practice, however their construction is very complicated and time consuming and therefore expensive.

SUMMARY OF THE INVENTION

Moving on from this the invention is based on the exercise of improving a medical instrument of the above mentioned type so that the force-limiting device is simple and cost effective to construct.

The solution to this exercise according to the invention is characterised by the push/pull rod being designed with spring-like elasticity along the line of displacement and thus creating the force-limiting device.

By configuring the push/pull rod as a spring-like elastic component it is possible to produce a medical instrument with a force-limiting device without additional components for the first time.

In accordance with the first embodiment configuration the push/pull rod is designed with at least sectional undulatory curves to provide the spring-like elasticity. This configuration provides the opportunity for the push/pull rod to elongate itself, preferably reversibly, in the area of the undulatory curve in the event of being subjected to excess tensile pressure.

In order to avoid the push/pull rod from jumping from one side of the inner wall of the hollow cylindrical shaft to the other under tensile pressure, the invention furthermore suggests that the undulatory curves of the individual sections be designed offset on planes from one another, so that the push/pull rod can be guided through the inside of the hollow shaft tube in all directions. It suggests that the each of the sections with individual undulatory curves preferably be designed on planes, offset at 90° from one another. This embodiment configuration is simple to manufacture by placing the push/pull rod repeatedly into a press.

The invention further suggests an embodiment configuration in which the semi-curves of the undulatory curves creating the undulating force-limiting device are offset at 90° or 135° from one another.

The spring-like elasticity of the push/pull rod can in one configuration of the invention be adjusted through its shape and the number of undulatory curves go that it is possible for the force-limiting device to be adapted to the respective necessary and appropriate closing pressure.

A second embodiment configuration of the invention suggests that the push/pull rod be designed with at least sectional turned spiral coils to provide the spring-like elasticity. Along with the creation of the undulatory curves, the spiral coil configuration of the push/pull rod offers the opportunity for the push/pull rod to flexibly elongate itself in the event of excess tensile pressure.

With this embodiment configuration the spring-like elasticity of the push/pull rod is preferably adjusted through the gradient of the turned spiral coil sections, in which the turned spiral coil sections preferably have a large gradient.

Finally the invention suggests that the spring-like elasticity of the push/pull rod can be adjusted by way of the material used for the push/pull rod.

Further, for technical and production reasons as well as for increasing operational safety, it is suggested that the push/pull rod be made of one uniform piece of material and/or with a virtually constant cross section.

BRIEF DESCRIPTION OF THE DRAWINGS

Further characteristics and advantages of the invention can be extracted from the following description of the associated diagram, in which the one embodiment configuration for creating a force-limiting device for a medical instrument according to the invention is depicted. The diagrams show:

FIG. 2a  a side view of a force-limiting device of a medical instrument per FIG. 1 with undulatory curved sections, and
FIG. 2b  a side view of the force-limiting device per FIG. 2a, however rotated 90°.

DETAILED DESCRIPTION OF THE INVENTION

Figure 1:
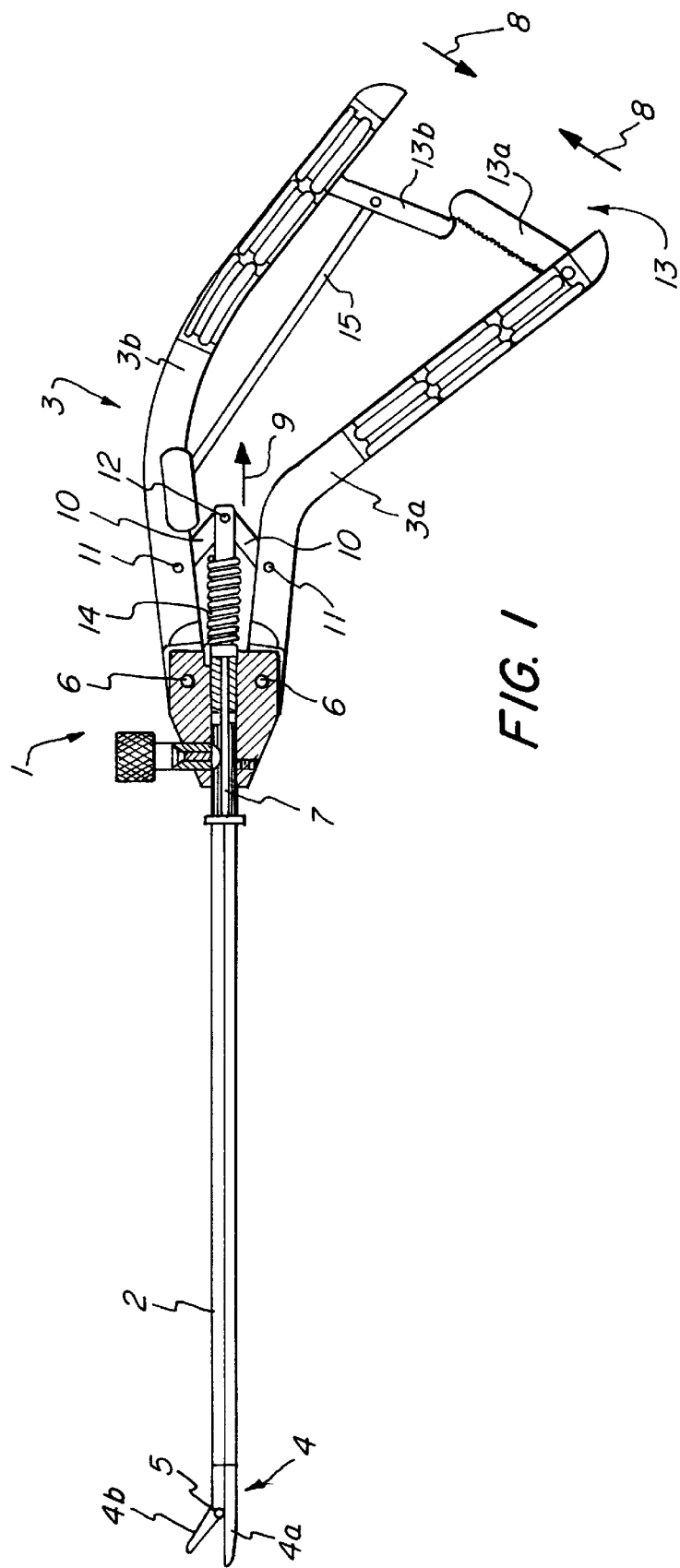
FIG. 1   is a side view of a surgical instrument according to the invention in the form of a gripping tool.

FIG. 1 depicts a surgical instrument in the form of a gripping tool 1. The gripping tool 1 has a hollow cylindrical shaft 2 along its lateral length, on the proximal end of which a hard manipulator 3 is located, and on the distal end of which remote tool parts 4 are arranged in the form of two open-ended sections and which can be activated via the hand manipulator 3 of the gripping tool 1.

The remote tool parts 4 are designed so that one remote tool part 4a is rigidly connected to the shaft 2, whilst the other remote tool part 4b is located and can swivel on an axis 5 across from the rigid remote tool part 4a. Understandably it is also possible for both remote tool parts 4 to be designed to swivel.

The hand manipulator 3 for activating the remote tool parts 4 has two handle elements 3a and 3b which swivel on hinge axes 6 across from the shaft 2.

The connection between the hand manipulator 3—more precisely the swivelling handle elements 3a and 3b of the hand manipulator 3—and the swivelling remote tool parts 4b of the remote tool part 4 is provided via a push/pull rod 7 located and guided inside the hollow cylindrical shaft 2.

If the gripping tool 1 is grabbed in the open position depicted in FIG. 1, whereupon the handle elements 3a and 3b of the hand manipulator 3 are encompassed by the operator's hand, it is necessary, in order to guide the remote tool part 4 into grabbing position, to manipulate the swivelling handle elements 3a and 3b towards one another in the direction of arrow 8, through which action the push/pull rod 7 is proximally displaced in a line with the arrow 9, and which furthermore leads to the swivelling remote tool part 4b being displaced in the direction of the closed position.

Activation of the push/pull rod 7 via the handle elements 3a, 3b of the hand manipulator 3 is carried out via control levers 10 which, forming a parallelogram on the one hand, are located on the hand grips 3a, 3b and which swivel at the knuckle joints 11 and on the other hand are located at a pivot point 12 on the push/pull rod 7.

In order to determine on the one hand the position of the two handle elements 3a and 3b to one another and therefore the respective remote tool parts 4a and 4b, and on the other hand to independently guide the handle elements 3a and 3b into their open base position again according to FIG. 1, the gripping tool 1 depicted has on the one hand a locking device 13, via which the handle elements 3a and 3b can be interlocked with one another, and which on the other hand has a spiral coiled spring 14 arranged on the proximal end of the push/pull rod 7. When the handle elements 3a, 3b are pressed together, the spiral coil spring 14 is elongated. The locking device 13 depicted for fixing the handle elements 3a, 3b comprises a draw rod 13a and a lock clip 13b which are each connected to one handle element 3a, 3b facing one another.

As soon as the lock clip of the locking device 13 is lifted via a releasing mechanism 15, the spiral coil spring 14 recoils and pushes the handle elements 3a and 3b apart again into the base position by way of the two control levers 10, as depicted in FIG. 1.

As can be seen in FIG. 1 the distance from the outer end of the swivelling handle elements 3a, 3b to the knuckle joint 11 of the control levers 10 connected to the push/pull rod 7 is very much greater than the distance between the knuckle joints 11 and the pivot point 12 for the control levers 10 on the push/pull rod 7. In this way the force which is exerted by the hand onto the swivelling handle elements 3a, 3b is amplified due to mechanical leverage, wherein the normal transmission ratio is about 10:1. With a normal closing force of about 100 N the exerted force on the push/pull rod 7 is about 1,000 N after tenfold amplification.

However a hand can also exert considerably greater force than 150 N or more, therefore the gripping tool 1 depicted has a force-limiting device 16, which is depicted in more detail in FIGS. 2a and 2b. The force-limiting device 16 is there to prevent undue excess force being exerted onto the remote tool parts 4 via the push/pull rod 7 which can lead to damage or even fracturing of the remote tool parts 4.

In the diagrams in FIG. 2a and FIG. 2b a configuration of the force-limiting device 16 is depicted which totally eliminates additional components since, according to this embodiment configuration, the push/pull rod 7 simultaneously assumes the same function as the force-limiting device 16. To this end the push/pull rod 7 is designed to have spring-like elasticity along its line of displacement within the hollow cylindrical shaft 2, so that the push/pull rod 7 can be retracted and/or elongated with increasing tension in order to absorb excess forces and to block them from the reaching the remote tool parts.

In the embodiment configuration depicted with a spring-like elastic push/pull rod 7, the spring-like elasticity is achieved by designing the push/pull rod 7 with sectional undulatory curves along its total length. The opportunity exists for the push/pull rod 7 to flexibly distort in the area of the individual undulatory curves 17 and thereby partially transfer the force exerted onto the push/pull rod 7 into this distortion task.

In order to prevent the push/pull rod 7 from jumping from one side wall to the other side wall within the hollow cylindrical shaft 2 under tensile pressure when the undulatory curve 17 is designed on just one plane, the individual sections of the undulatory curves 17 are designed offset at 90° from one another respectively as depicted in FIGS. 2a and 2b.

With this embodiment configuration the spring-like elasticity of the push/pull rod 7 can be adapted and determined by way of the type and number of undulatory curves 17 as well as the choice of material for the push/pull rod 7.

Along with the embodiment configuration depicted, in which the undulatory curves 17 can be simply and advantageously manufactured, singly or multiply, by laying the straight push/pull rod 7 in a press, the spring-like elasticity of the push/pull rod 7 can also be achieved by the push/pull rod 7 at least being designed with sectional turned spiral coils. With this embodiment configuration (not illustrated) the spring-like elasticity of the push/pull rod 7 can be adapted through the choice of material for the push/pull rod 7 as well as through the gradient of the turned spiral coils, wherein a greater gradient is seen as preferential.

The force-limiting device 16 depicted in FIGS. 2a and 2b is distinguished by being simple and cost effective to manufacture without additional components.

What is claimed is:

1. A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement.

2. A medical instrument according to claim 1, wherein said push/pull rod is designed to have at least sectional undulatory curves to provide said spring-like elasticity.

3. A medical instrument according to claim 2, wherein said individual sections with the undulatory curves are designed on planes offset from one another.

4. A medical instrument according to claim 3, wherein said individual sections with the undulatory curves are each designed on planes offset at 90° from one another.

5. A medical instrument according to claim 2, wherein said individual semi-curves of said sections with the undulatory curves are designed to be offset at 90° or 135° from one another.

6. A medical instrument according to claim 2, wherein the spring-like elasticity of said push/pull rod can be adjusted through its shape and/or the number of the undulatory curves.

7. A medical instrument according to claim 1, wherein said push/pull rod is designed with at least turned spring coil sections to provide the spring-like elasticity.

8. A medical instrument according to claim 7, wherein the spring-like elasticity of said push/pull rod can be adjusted through the gradient of said turned spring coil sections.

9. A medical instrument according to claim 7, wherein said turned spring coil sections have a large gradient.

10. A medical instrument according to claim 1, wherein the spring-like elasticity of said push/pull rod can be adjusted via the material of said push/pull rod.

11. A medical instrument according to claim 1, wherein said push/pull rod is made from one uniform piece of material.

12. A medical instrument according to claim 1, wherein said push/pull rod has a virtually constant cross section.

* * * * *

UNITED STATES PATENT AND TRADEMARK OFFICE
CERTIFICATE OF CORRECTION

PATENT NO.     : 6,589,259 B1
DATED          : July 8, 2003
INVENTOR(S)    : Simon Solingen It is certified that error appears in the above-identified patent and that said Letters Patent is hereby corrected as shown below:

<u>Title page,</u>
Item [54], Title, should read:
-- [54] A MEDICAL INSTRUMENT HAVING A FORCE-LIMITING DEVICE --.

Signed and Sealed this

Thirtieth Day of September, 2003

JAMES E. ROGAN
*Director of the United States Patent and Trademark Office*

Disclaimer

6,589,259-C1—Simon Solingen, Los Angeles, CA (US); MEDICAL INSTRUMENT HAVING A FORCE-LIMITING DEVICE, Patent dated Dec. 15, 2009. Disclaimer filed Oct. 13, 2011, by the Assignee, Karl Storz GmbH & Co. KG.
Hereby enters this disclaimer to claims 2,6,10, 13-17 and 19-28 of said patent.

(*Official Gazette January 24, 2012*)

(12) EX PARTE REEXAMINATION CERTIFICATE (7242nd)
United States Patent
Solingen

(10) Number: US 6,589,259 C1
(45) Certificate Issued: Dec. 15, 2009

(54) MEDICAL INSTRUMENT HAVING A FORCE-LIMITING DEVICE

(75) Inventor: Simon Solingen, Los Angeles, CA (US)

(73) Assignee: Karl Storz GmbH & Co. KG, Tuttlingen (DE)

Reexamination Request:
No. 90/007,852, Dec. 19, 2005

Reexamination Certificate for:
Patent No.: 6,589,259
Issued: Jul. 8, 2003
Appl. No.: 09/473,502
Filed: Dec. 28, 1999

Certificate of Correction issued Sep. 30, 2003.

(51) Int. Cl.
*A61B 17/28* (2006.01)
*A61B 19/00* (2006.01)
*A61B 17/32* (2006.01)

(52) U.S. Cl. ...................................... 606/170
(58) Field of Classification Search .............. None
See application file for complete search history.

(56) References Cited

U.S. PATENT DOCUMENTS

| 4,122,856 A | | 10/1978 | Mosior et al. |
| 5,254,130 A | * | 10/1993 | Poncet et al. ............... 606/206 |
| 5,413,583 A | | 5/1995 | Wohlers |
| 5,490,861 A | | 2/1996 | Kratsch et al. |
| 5,496,347 A | | 3/1996 | Hashiguchi et al. |
| 5,562,699 A | | 10/1996 | Heimberger et al. |
| 5,683,412 A | | 11/1997 | Scarfone |
| 6,096,058 A | * | 8/2000 | Boche ........................ 606/205 |

FOREIGN PATENT DOCUMENTS

DE 197 31 453 C2 2/2002

\* cited by examiner

*Primary Examiner*—David O. Reip

(57) ABSTRACT

The invention relates to a medical instrument, particularly a surgical instrument with a displaceable push/pull rod arranged on the proximal end of a hand manipulator for activating remote tool parts on the distal end, in which a force-limiting device is envisaged for limiting the transmission of force onto the remote tool parts from the hand manipulator via the push/pull rod. In order to design a simple and cost effective force-limiting device the push/pull rod is designed to be spring elastic in its lateral length.

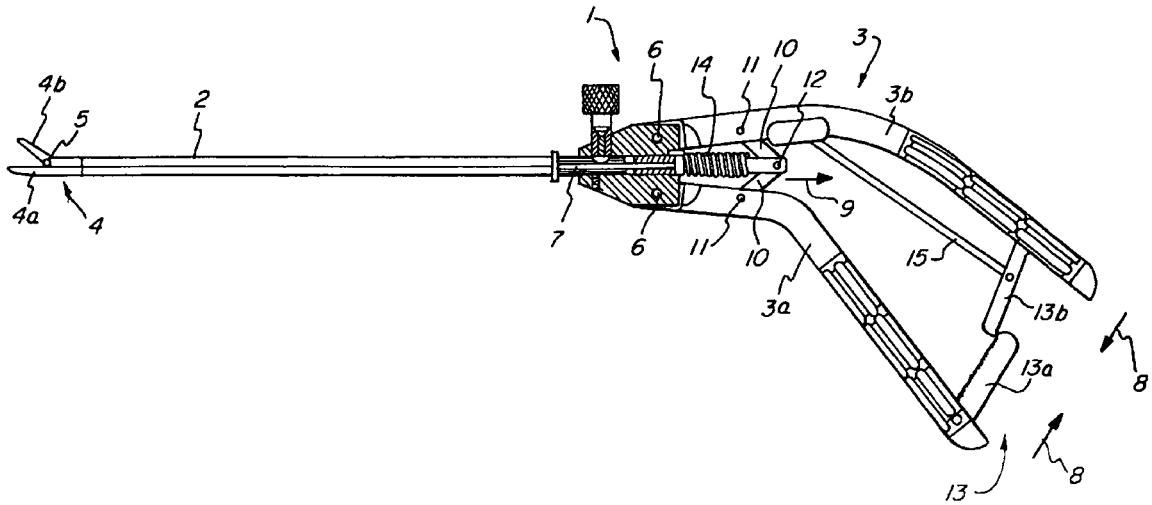

US 6,589,259 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2 and 6–10 is confirmed.

Claims 1, 11 and 12 are cancelled.

Claims 3 and 5 are determined to be patentable as amended.

Claim 4, dependent on an amended claim, is determined to be patentable.

New claims 13–28 are added and determined to be patentable.

3. [A medical instrument according to claim 2] *A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein said push/pull rod is designed to have at least sectional undulatory curves to provide said spring-like elasticity,* wherein [said] individual sections with the undulatory curves are designed on planes offset from one another.

5. [A medical instrument according to claim 2] *A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein said push/pull rod is designed to have at least sectional undulatory curves to provide said spring-like elasticity,* wherein [said] individual semi-curves of [said] sections with the undulatory curves are designed to be offset at 90° or 135° from one another.

*13. A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein said push/pull rod is designed to have at least sectional undulatory curves to provide said spring-like elasticity, wherein the hand manipulator comprises two handle elements and an axis of rotation for movement of at least one handle element relative to the other handle element, wherein the at least one handle element has a distal end and a proximal end, wherein the distal end of the at least one handle element is located closer to said push/pull rod than the proximal end of the at least one handle element, wherein the axis of rotation of the at least one handle element is located closer to the distal end than to the proximal end of the at least one handle element.*

*14. A medical instrument comprising a push/pull rod displaceable by a hand manipulator arranged on a proximal end of said push/pull rod for activating remote tool parts at a distal end of said push/pull rod, said push/pull rod disposed within the medical instrument to transmit a pulling force onto said remote tool parts from said hand manipulator to close said remote tool parts and a pushing force onto said remote tool parts from said hand manipulator to open said remote tool parts, said medical instrument further comprising a force-limited device envisaged for limiting the transmission of force onto said remote tool parts from said hand manipulator via said push/pull rod, wherein said push/pull rod itself is designed to form said force-limiting device having spring-like elasticity along the line of displacement, and wherein said push/pull rod is designed to have at least sectional undulatory curves to provide said spring-like elasticity.*

*15. A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein said push/pull rod is designed to have at least sectional undulatory curves to provide said spring-like elasticity, wherein said hand manipulator comprises two handle elements and an axis of rotation for movement of at least one movable hand element relative to the other handle element, said movable handle element having a first end for manipulation by a user and a second end for attachment to said push/pull rod, said axis being positioned closer to said second end than to said first end.*

*16. A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein said push/pull rod is designed to have at least sectional undulatory curves to provide said spring-like elasticity, wherein said hand manipulator is capable of being in an open position and in a closed position and comprises two handle elements, each handle element having a first distal end and a second proximal end, wherein the first ends are located closer to the push/pull rod than the second* proximal ends, and wherein the first distal ends are more closely disposed relative to each other that the second proximal ends when said hand manipulator is in the open position.

17. A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein said push/pull rod is designed to have at least sectional undulatory curves to provide said spring-like elasticity, wherein said hand manipulator is capable of being in an open position and in a closed position and comprises two handle elements, wherein the handle elements are less outwardly spaced apart in their distal aspect than in their proximal aspect when said hand manipulator is in the open position.

18. A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein the hand manipulator comprises an axis of rotation, a first handle element having a first proximal end and a second handle element having a second proximal end, wherein the first proximal end is located further from the remote tool parts in a direction along the line of displacement than the second proximal end, and wherein the first handle element is movable about the axis of rotation.

19. A medical instrument comprising a push/pull rod displaceable by a hand manipulator arranged on a proximal end of said push/pull rod for activating remote tool parts at a distal end of said push/pull rod, said medical instrument further comprising a force-limiting device envisaged for limiting the transmission of force onto said remote tool parts from said hand manipulator via said push/pull rod, wherein said push/pull rod itself is designed to form said force-limiting device having spring-like elasticity along the line of displacement, wherein said push/pull rod comprises an axis along the line of displacement, at least one portion that extends away from the axis in a first direction and at least one other portion that extends away from the axis in a direction substantially opposite to the first direction.

20. A medical instrument according to claim 18, wherein said push/pull rod comprises an axis along the line of displacement, at least one portion that extends away from the axis in a first direction and at least one other portion that extends away from the axis in a direction substantially opposite to the first direction.

21. A medical instrument according to claim 20, wherein the at least one portion and at least one other portion provide spring-like elasticity along the line of displacement.

22. A medical instrument according to claim 19, wherein the at least one portion and at least one other portion provide spring-like elasticity along the line of displacement.

23. A medical instrument according to claim 1, wherein said push/pull rod comprises an axis along the line of displacement of said push/pull rod, wherein said push pull rod extends away from and back to the axis at least one time.

24. A medical instrument according to claim 1, wherein said push/pull rod comprises an axis along the line of displacement of said push/pull rod, wherein said push pull rod extends away from and back to the axis at least two times.

25. A medical instrument according to claim 1, wherein said push/pull rod comprises an axis along the line of displacement of said push/pull rod, wherein said push pull rod extends away from and back to the axis at least three times.

26. A medical instrument according to claim 23, wherein the extending at least one time of the push/pull rod away from and back to the axis provides spring-like elasticity.

27. A medical instrument according to claim 24, wherein the extending at least two times of the push/pull rod away from and back to the axis provides spring-like elasticity.

28. A medical instrument according to claim 25, wherein the extending at least three times of the push/pull rod away from and back to the axis provides spring-like elasticity.

\* \* \* \* \*